US00PP37083P2

(12) United States Plant Patent
Chaussard

(10) Patent No.: US PP37,083 P2
(45) Date of Patent: Nov. 4, 2025

(54) ***CAMPSIS* PLANT NAMED 'MINCAMROUG13'**

(50) Latin Name: ***Campsis radicans* x *grandiflora***
Varietal Denomination: MINCAMROUG13

(71) Applicant: Hortival Diffusion, Beaufort en Anjou (FR)

(72) Inventor: Pierre Chaussard, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 16 days.

(21) Appl. No.: 18/930,487

(22) Filed: Oct. 29, 2024

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Campsis* plant named 'MINCAMROUG13' is disclosed, characterized by red colored flowers of medium size. Plants have a vigorous climbing habit. Foliage is dark green, turning a distinct dark greyed-purple in the Fall. The new variety is a *Campsis*, normally produced as an outdoor garden plant.

5 Drawing Sheets

Latin name of the genus and species: *Campsis radicans* x *grandiflora*.

Variety denomination: 'MINCAMROUG13'.

BACKGROUND OF THE INVENTION

The present invention comprises a new and distinct variety of *Campsis*, hereinafter referred to by the cultivar name 'MINCAMROUG13'. This new *Campsis* was developed through a breeding program by the inventor at a nursery in La Menitre, France, by cross-pollination of the unpatented seed parent, *Campsis radicans* 'Stromboli'. The pollen parent is an unnamed, unpatented variety of *Campsis grandiflora*. The cross-pollination date resulting in the new variety was performed in July of 2005.

The new variety was found and selected in October of 2009. The first asexual propagation of 'MINCAMROUG13' was carried out in January of 2010 by softwood cuttings at the same nursery in La Menitre, France. 'MINCAMROUG13' has been found to retain its distinctive characteristics through successive asexual propagations. Multiple generations have been propagated, with the new variety characteristics reproduced true to type.

An application (2024/1609) has been filed with the CPVO by Hortival Diffusion Jul. 8, 2024. Hortival Diffusion is the employer of the inventor and assignee of the entire rights of this application.

SUMMARY OF THE INVENTION

The following traits have been repeatedly observed and are determined to be the unique characteristics of *Campsis* 'MINCAMROUG13'. These characteristics in combination distinguish 'MINCAMROUG13' as a new and distinct *Campsis* cultivar:

1. Red colored flower of medium size.
2. Dark green foliage turning a distinct dark-greyed-purple in the Fall.

3. Dark Greyed-Purple colored branches.
4. Vigorous climbing habit.

PARENT COMPARISON

'MINCAMROUG13' is similar to the seed parent in most horticultural characteristics. 'MINCAMROUG13' however differs in the following:

1. Flower size of the new cultivar is larger than flower size of the seed parent.
2. Plants of new cultivar grow faster and climb more vigorously than plants of the seed parent.
3. Flower buds of the new cultivar are elliptic; flower buds of the seed parent are globular.
4. Fall branch color of the new cultivar is darker than that of the seed parent.

'MINCAMROUG13' is similar to the pollen parent in most horticultural characteristics. 'MINCAMROUG13' however differs in the following:

1. Flower size of the new cultivar is smaller than flower size of the pollen parent.
2. Plants of new cultivar grow faster and climb more vigorously than plants of the pollen parent.
3. Flower color of the new cultivar is red; flower color of the pollen parent is orange.

COMMERCIAL COMPARISON

*Campsis* 'MINCAMROUG13' can be compared to the commercial variety *Campsis* 'Hoch128' U.S. Plant Pat. No. 34,699.

1. Plants of the 'MINCAMROUG13' are approximately 30% taller and almost twice as wide as plants of 'Hoch128'.
2. Stems of 'MINCAMROUG13' are distinctively colored Greyed-Purple N187A; stems of 'Hoch 128' are Green and Yellow-Green.

3. Corolla tube length of 'MINCAMROUG13' is approximately half that of 'Hoch128'.
4. Petiole length of 'MINCAMROUG13' is approximately double that of 'Hoch128'.

BRIEF DESCRIPTION OF THE PHOTOGRAPHS

This new *Campsis* is illustrated by the accompanying photographs which show the plant's form, foliage and inflorescences. The colors shown are as true as can be reasonably obtained by conventional photographic procedures. Plants were grown in La Menitre, France.

FIG. 1. Shows a flowering plant of 'MINCAMROUG13' in a 4-liter pot at approximately 1-year old during Summer.

FIG. 2. Shows a close-up view of flowers of the new cultivar during the Summer.

DETAILED BOTANICAL DESCRIPTION

Figure 1:
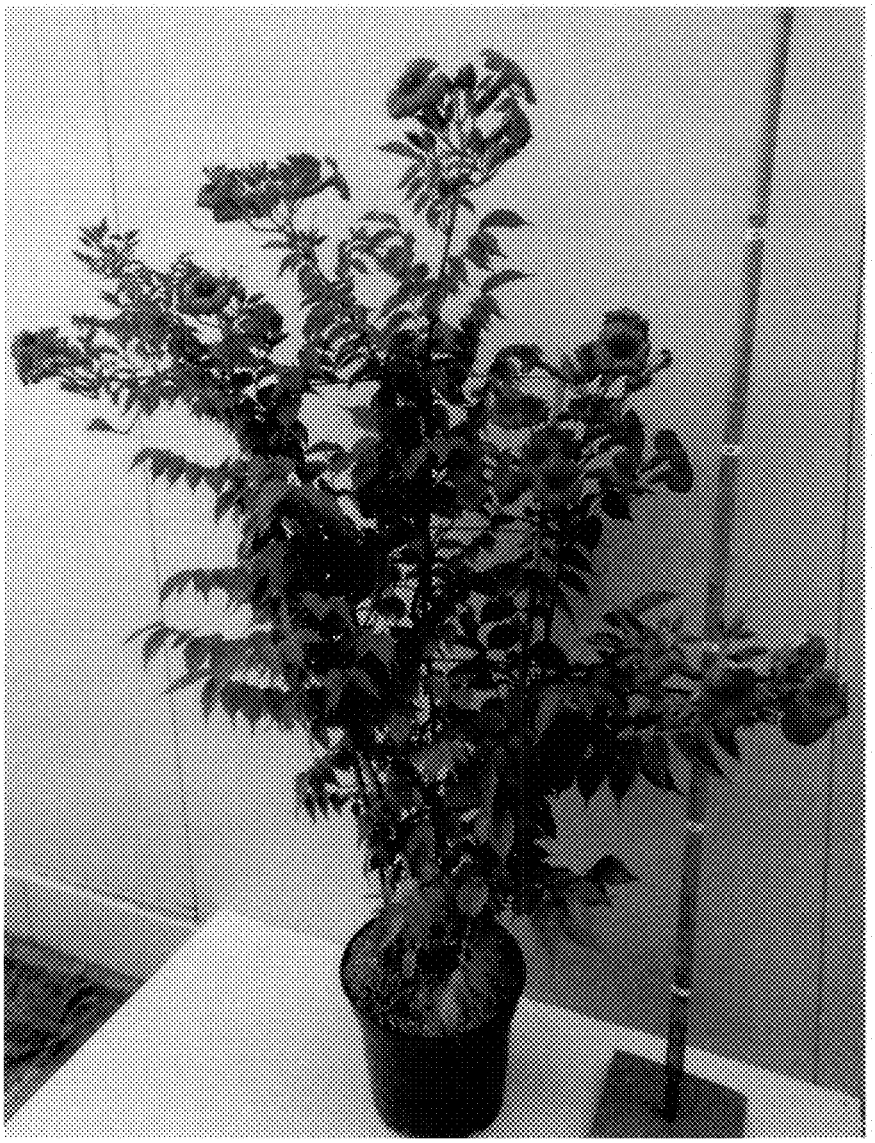
Figure 2:
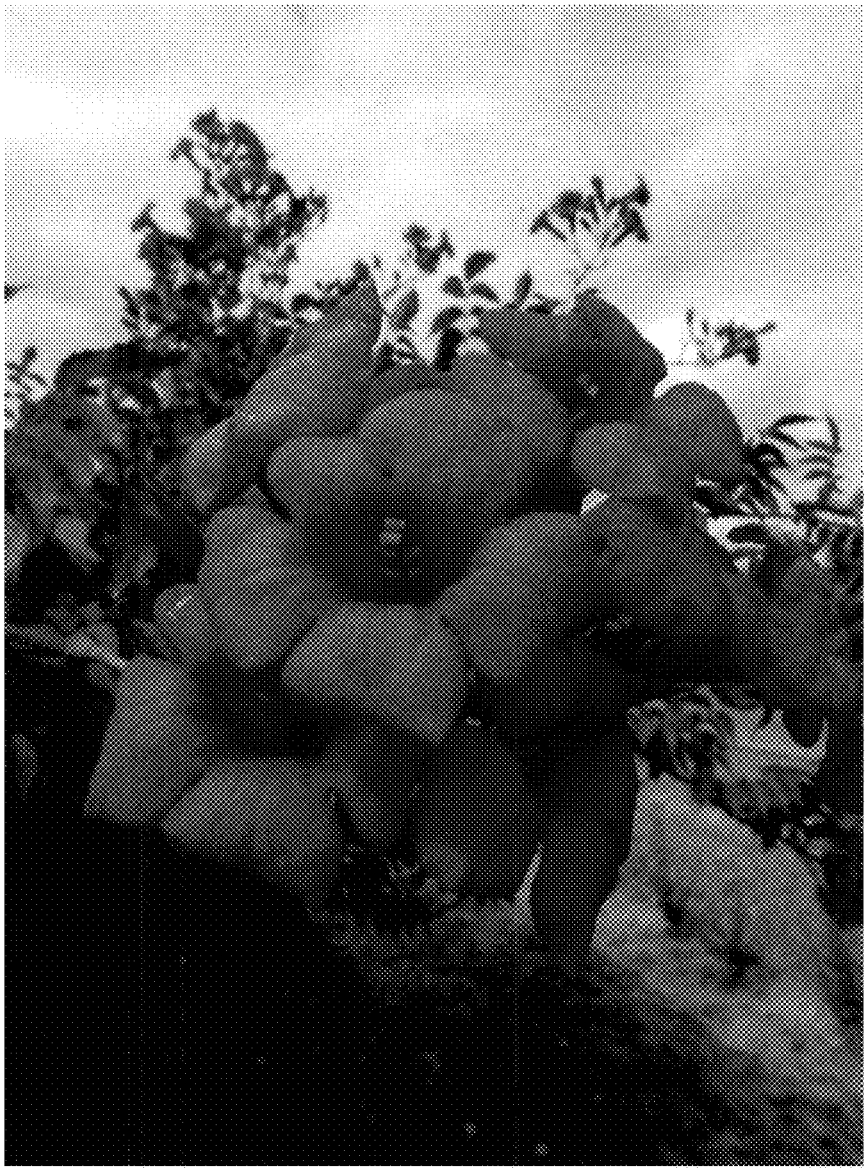
Figure 3:
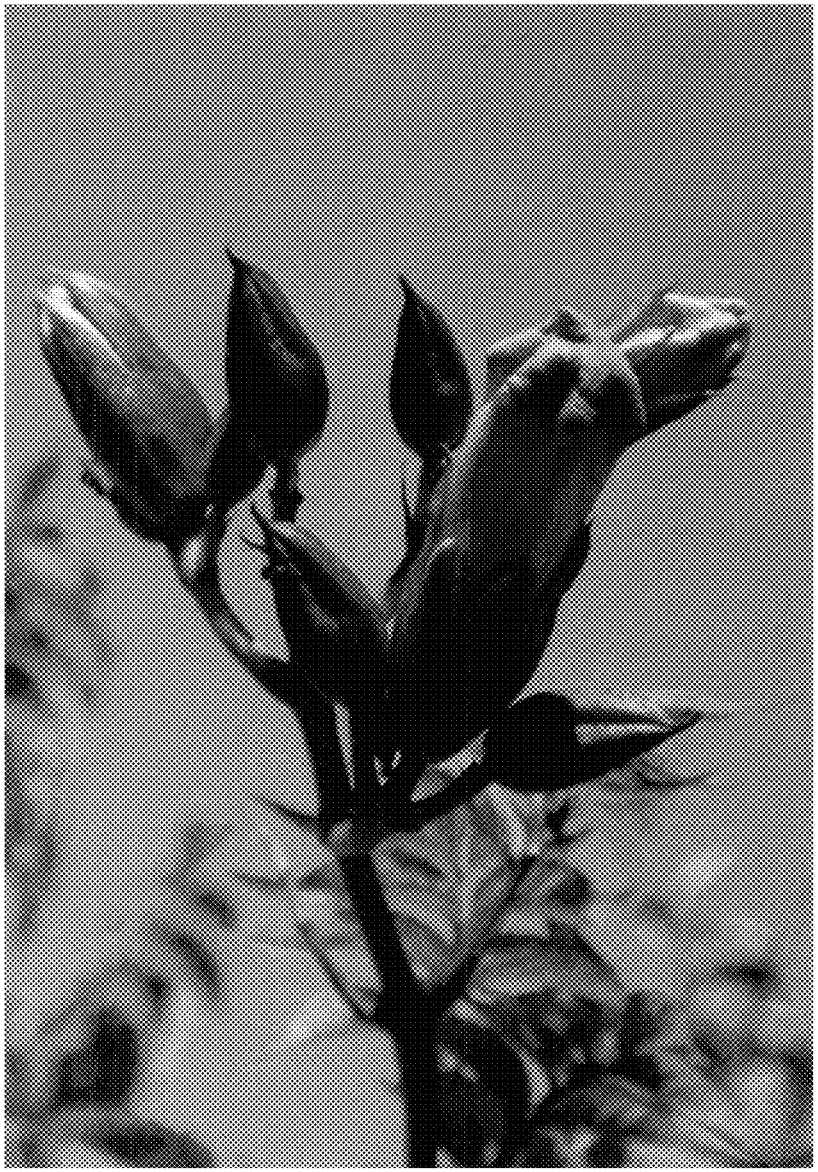
FIG. 3 illustrates flower buds of 'MINCAMROUG13'.
Figure 4:
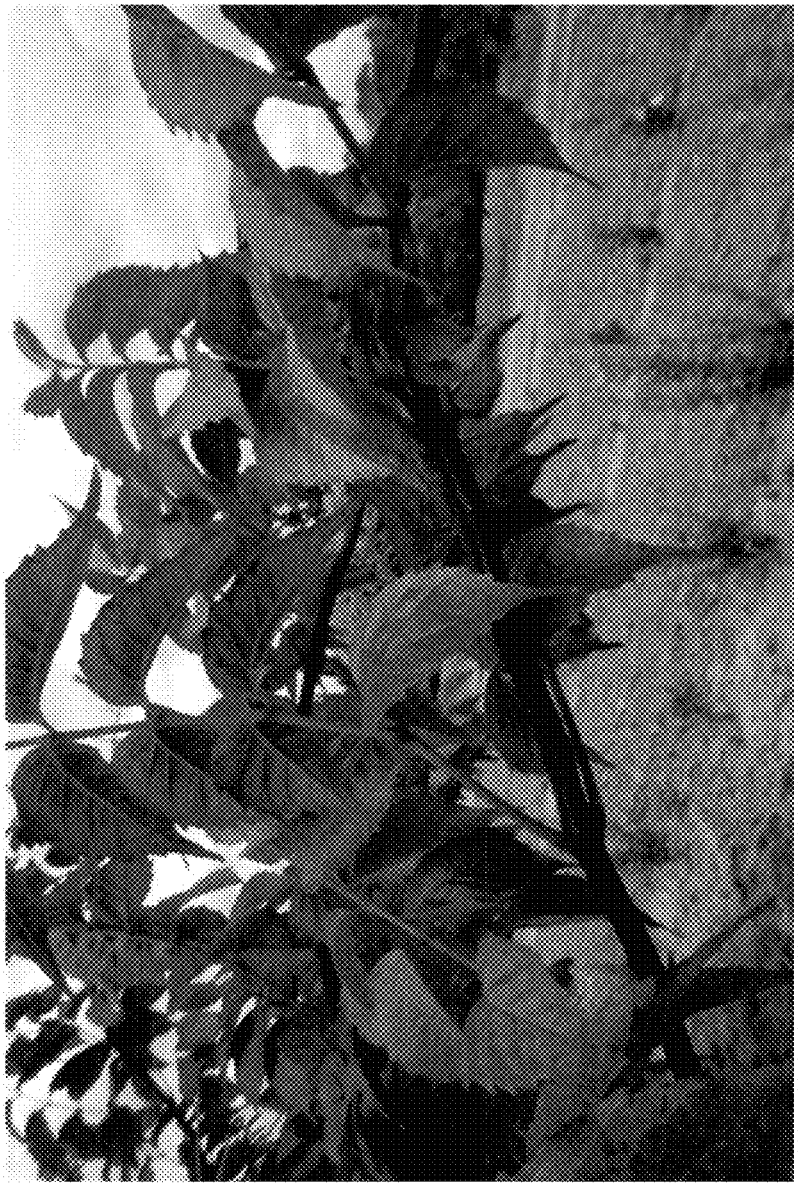
FIG. 4 illustrates in full color the beginning of the Fall color foliage change.
Figure 5:
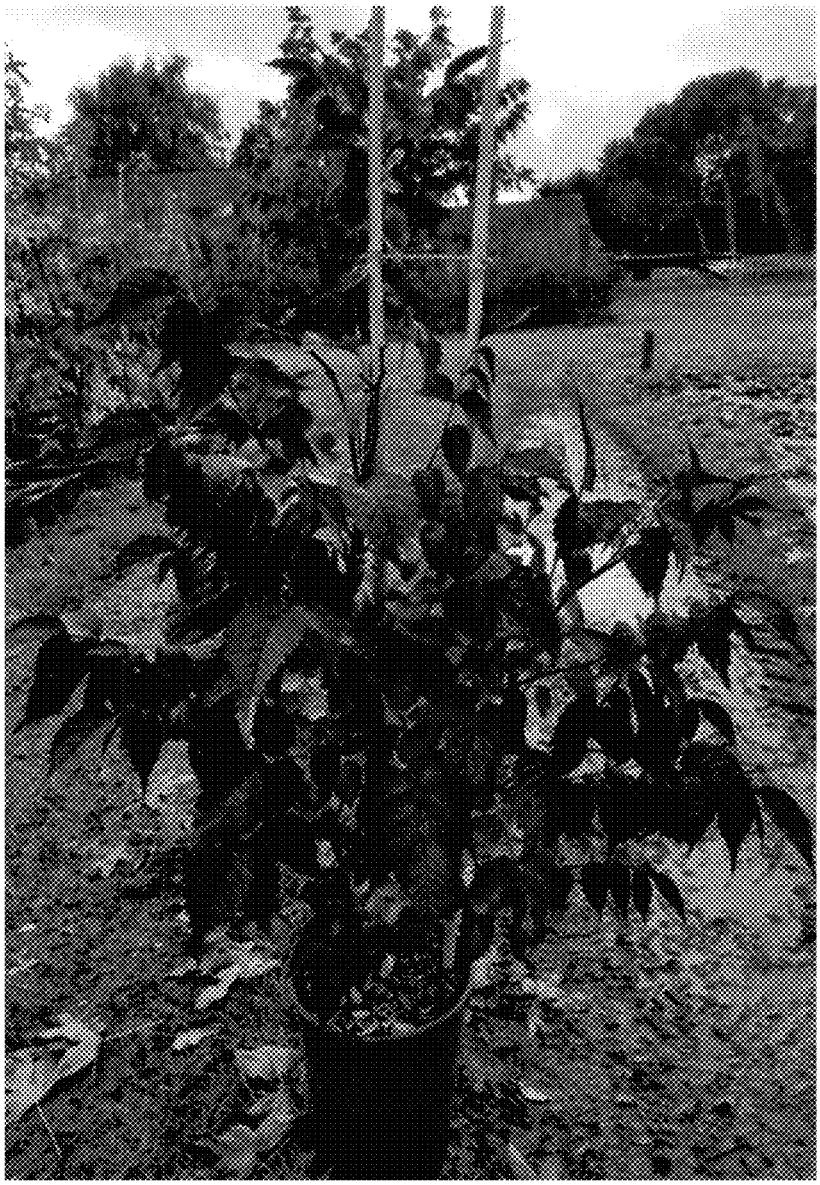
FIG. 5 illustrates the Fall foliage color in October.

In the following description, color references are made to The Royal Horticultural Society Colour Chart 2015 except where general terms of ordinary dictionary significance are used. The following observations and measurements describe 'MINCAMROUG13' plants grown outdoors in La Menitre, France. The growing temperature during July and August ranged from 13° C. to 39° C. during the day and from 10° C. to 26° C. during the night. General light conditions are natural sunlight. Measurements and numerical values represent averages of typical plant types.

Botanical classification: *Campsis radicans* x *grandiflora* 'MINCAMROUG13'.

PROPAGATION

Typical method: Softwood cuttings.

Time to initiate rooting: 5 to 7 days in summer at approximately 18° C. to 27° C.

Time to produce a rooted young plant: 3 weeks in summer at approximately 18° C. to 27° C.

Root description: Moderately dense, fibrous. Tan in color, not accurately measured with an R.H.S. chart.

PLANT

Plant type: Flowering woody climber.

Age of plant described: 400 days from a rooted cutting.

Growth habit: Climbing.

Height: 94 cm.

Plant spread: 60 cm.

Growth rate: Rapid.

Plant vigor: Highly vigorous.

Branching characteristics: One main stem, 4 primary laterals.

Branching habit: Moderately well branched. Lower lateral occurring at about 45 degree angles from the main stem. Upper lateral occurring at angles between approximately 35 degrees and 45 degrees from center.

Characteristics of main stem:

*Form*.—Ovate.
*Length*.—81 cm.
*Diameter*.—9 mm.
*Color*.—Greyed-Purple N187A.
*Texture*.—Woody, slightly scaly.
*Strength*.—Strong.

Quantity of primary lateral branches: About 4.

*Form*.—Ovate.
*Length*.—26 cm.
*Diameter*.—5 mm.
*Color*.—Yellow-Green N144 C in summer, Brown 200A in Fall.
*Texture*.—Glabrous.
*Strength*.—Strong.

FOLIAGE

Leaf:

*Arrangement*.—Opposite.
*Quantity per plant*.—Average 62.
*Leaf type*.—Compound pinnate.
*Average leaf length*.—Approximately 27 cm.
*Average leaf width*.—Approximately 15 cm.
*Overall leaf shape*.—Ovate.
*Leaf aspect*.—Flat.

Leaflets:

*Leaflets per leaf*.—Average 10.
*Average leaflet length*.—Approximately 8 cm.
*Average leaflet width*.—Approximately 4 cm.
*Leaflet shape*.—Oblanceolate.
*Leaflet apex*.—Acute.
*Leaflet base*.—Attenuate.
*Margin*.—Serrulate.
*Aspect*.—Slightly convex.
*Texture of top surface*.—Glabrous.
*Texture of bottom surface*.—Slightly pubescent.
*Color*.—Young foliage upper side: Yellow-Green 146A slight margin Greyed-Purple 187A (strongest on distal leaflets). Young foliage under side: Yellow-Green 146B. Mature foliage upper side: Green 137A. Mature foliage under side: Yellow-Green 146C. Fall foliage upper side: Greyed-Purple N186C. Fall foliage under side: Greyed-Purple N186D.
*Venation*.—Type: Pinnate. Venation color upper side: Yellow-Green 153 B. Venation color under side: Yellow-Green 145C. Petiole: Length: 7 cm. Diameter: 3 mm. Color: Greyed-Purple 183A. Texture: Glabrous.
*Leaflet petiole*.—Length: Approximately 6 mm. Width: 1 mm. Color: Upper side Green 137A, margins/sides Greyed-Purple 183A, under side Yellow-Green 145C. Texture: Glabrous.

FLOWER

Natural flowering season: Mid-summer through early Fall.

Inflorescence (cyme): Terminal cluster of single flowers, blooms on current year's growth.

*Height*.—29 cm.
*Diameter*.—20 cm.
*Quantity of bud flowers per plant* (*average range*).—53.

Individual flower (single trumpet shaped?): Single trumpet.

Rate of flower opening: 8 to 14 days from bud to fully opened flower.

Flower longevity on plant: 2 to 3 days.

Persistent or self-cleaning: Self-cleaning.

Bud:

*Shape*.—Elliptic.
*Length* (*petals not visible*).—2.9 cm.

*Diameter* (*petals not visible*).—1 cm.
*Color*.—Greyed-Orange N163A just before opening, Yellow-Orange 21 C with petal color just beginning to show.

Flower size:
*Diameter*.—6 cm.
*Depth*.—5.8 cm. Throat Diameter: 1.8 cm. Tube Length: 5 cm. Tube Diameter at Base: 4.4 cm.

Petals:
*Quantity*.—5.
*Arrangement*.—Non-overlapping.
*Petal lobes*.—Length: 1.8 cm. Width: 2.6 cm. Shape: Flabellate witch lobes rounded.
*Apex*.—Rounded.
*Base*.—Fused.
*Margin*.—Entire.
*Texture, outer surfaces*.—Glabrous. Petal Lobe: Glabrous. Tube: Glabrous.
*Texture, inner surfaces*.—Glabrous. Petal Lobe: Glabrous. Tube: Glabrous. Throat: Glabrous.
*Color*.—Outer Surfaces: Petal Lobe when opening: Orange-Red 34C. Tube when opening: Orange-Red 31B. Petal Lobe fully opened: Orange-Red 34D. Tube fully opened: Orange-Red 34B. Petal Lobe fading: Orange-Red N34A. Tube fading: Orange-Red N34B. Inner Surfaces: Petal Lobe when opening: Red N45C. Tube when opening: Red N45C. Throat when opening: Red N45C. Petal Lobe fully opened: Red 46A. Tube fully opened: Red 45C with parallel striping of Orange-Red N34 A. Petal Lobe fading: Red 46A. Tube fading: Red 46A.

Sepals:
*Quantity*.—5.
*Arrangement*.—Fused into a single tube.
*Length*.—3 cm.
*Width*.—0.56 cm. Apex: Acute. Base: Fused.
*Margin*.—Entire.
*Color*.—Outer Surface: Greyed-Orange N172 A. Inner Surface: Yellow-Orange 18 B.
*Texture*.—Outer Surface: Glabrous. Inner Surface: Glabrous.

Peduncles:
*Length*.—4.3 cm.
*Diameter*.—0.37 cm.
*Angle*.—About 80° from the lateral branch.
*Strength*.—Strong.
*Texture*.—Glabrous.
*Color*.—Yellow-Green N144A.

Pedicels:
*Length*.—1 cm.
*Diameter*.—0.26 cm.
*Angle*.—About 40° to the lateral branch.
*Strength*.—Strong.
*Texture*.—Glabrous.
*Color*.—Yellow-Green N144A.

Fragrance: Not noticeable.
Nectaries: Not observed.

REPRODUCTIVE ORGANS

Stamens:
*Number*.—4 to 5.
*Filament length*.—2.2 cm.

Anthers:
*Shape*.—2-parted.
*Length*.—Approximately 0.3 cm.
*Color*.—Yellow 6A.
*Pollen*.—Color: Yellow 6A. Quantity: Abundant.

Pistil:
*Number*.—1.
*Length*.—4.8 cm.
*Style*.—Length: 3.6 cm. Color: Greyed-Purple 186C.
*Stigma*.—Shape: Flattened petaloid. Color: Greyed-Yellow 160A. Ovary Color: Green-Yellow 1C. Ovary length: 2.2 cm.

OTHER CHARACTERISTICS

Fruit: Green (RHS Green 143C turning 137A) and purple (Greyed-Purple N187A) pod. Pods about 10 to 14 cm long and 2.8 cm wide.

Disease and insect resistance: Neither resistance nor susceptibility to normal diseases and pests of *Campsis* observed. Typical diseases of *Campsis* include leaf spot fungi *Cercospora* and *Phyllosticta*. Powdery mildew caused by *Erysiphe* and *Microsphaera* can also be found on *Campsis* plants. Various whiteflies can infest *Campsis* plants, including *Bemisia argentifolii* and *Bemisia tabaci*.

Temperature range: USDA Zones 5-9.

What is claimed is:

1. A new and distinct cultivar of *Campsis* plant named 'MINCAMROUG13' as illustrated and described herein.

* * * * *